United States Patent
Guerra et al.

(10) Patent No.: US 9,266,999 B2
(45) Date of Patent: *Feb. 23, 2016

(54) OLIGOMERS AND CO-OLIGOMERS OF HIGHLY FLUORINATED SULFINIC ACID AND SALTS THEREOF

(75) Inventors: Miguel A. Guerra, Woodbury, MN (US); Gregg D. Dahlke, Saint Paul, MN (US); Denis Duchesne, Woodbury, MN (US); Tatsuo Fukushi, Woodbury, MN (US); Werner M. A. Grootaert, Oakdale, MN (US); Zai-Ming Qiu, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 234 days.

This patent is subject to a terminal disclaimer.

(21) Appl. No.: 13/995,037

(22) PCT Filed: Dec. 6, 2011

(86) PCT No.: PCT/US2011/063383
§ 371 (c)(1),
(2), (4) Date: Jun. 17, 2013

(87) PCT Pub. No.: WO2012/082454
PCT Pub. Date: Jun. 21, 2012

(65) Prior Publication Data
US 2013/0267658 A1 Oct. 10, 2013

Related U.S. Application Data

(60) Provisional application No. 61/424,153, filed on Dec. 17, 2010.

(51) Int. Cl.
| | | |
|---|---|---|
| C07C 313/02 | (2006.01) |
| C08G 61/00 | (2006.01) |
| C08F 8/44 | (2006.01) |
| C08F 14/18 | (2006.01) |
| C08F 214/18 | (2006.01) |

(52) U.S. Cl.
CPC . *C08G 61/00* (2013.01); *C08F 8/44* (2013.01); *C08F 14/18* (2013.01); *C07C 313/02* (2013.01); *C08F 214/184* (2013.01)

(58) Field of Classification Search
CPC ... C08G 61/00; C07C 313/02; C08F 214/184; C08F 14/18
See application file for complete search history.

(56) References Cited

U.S. PATENT DOCUMENTS

| | | | |
|---|---|---|---|
| 2,713,593 A | 7/1955 | Brice et al. | |
| 3,420,877 A | 1/1969 | Pavlik | |
| 4,151,053 A | 4/1979 | Fukumoto et al. | |
| 4,544,458 A | 10/1985 | Grot et al. | |
| 4,940,525 A * | 7/1990 | Ezzell et al. | 204/252 |
| 5,285,002 A * | 2/1994 | Grootaert | 526/222 |
| 2009/0221759 A1 | 9/2009 | Haring et al. | |

FOREIGN PATENT DOCUMENTS

| | | |
|---|---|---|
| CN | 101693751 A | 4/2010 |
| EP | 0 289 869 A2 | 11/1988 |
| JP | 56057832 A | 5/1981 |
| JP | 61185507 A | 8/1986 |

OTHER PUBLICATIONS

Fan-Hong et al., "Studies on sulfinatodehalogenation. XXIX. The sulfinatodehalogenation of primary polyfluoroalky iodides and bromides by sodium disulfite", Journal of Fluorine Chemistry, vol. 67, 1994, pp. 233-234.

Hu et al., "Reaction of Perfluoroalkanesulfinates with Allyl and Propargyl Halides, A Convenient Synthesis of 3-(Perfluoroalkyl) prop-1-enes and 3-(Perfluoroalkyl)allenes", Journal of Organic Chemistry, vol. 56, 1991, pp. 2801-2804.

Huang et al., "Perfluoroalkylation initiated with sodium dithionite and related reagent systems", Journal of Fluorine Chemistry, vol. 58, 1992, pp. 1-8.

Huang et al., "Studies on Sulfinatodehalogenation, IV. The sulfinatodebromination of primary perfluoroalkyl bromides and perfluoroalkylene α ω-dibromides", Acta Chimica Sinica, No. 1, 1986, pp. 68-72.

Huang et al., "Studies on Sulfinatodehalogenation, VIII. Sodium dithionite-initiated perfluoroalkyl radical addition on double bond", Acta Chimica Sinica, No. 2, 1986, pp. 178-184.

* cited by examiner

*Primary Examiner* — Michael Pepitone
(74) *Attorney, Agent, or Firm* — C. Michael Geise

(57) ABSTRACT

There is provided oligomers comprising a highly fluorinated sulfinate oligomers.

14 Claims, No Drawings

OLIGOMERS AND CO-OLIGOMERS OF HIGHLY FLUORINATED SULFINIC ACID AND SALTS THEREOF

CROSS REFERENCE TO RELATED APPLICATIONS

This application is a national stage filing under 35 U.S.C. 371 of PCT/US2011/063383, filed Dec. 6, 2011, which claims priority to Provisional Application No. 61/424,153, filed Dec. 17, 2010, the disclosure of which is incorporated by reference in its/their entirety herein.

The present disclosure relates to highly fluorinated sulfinic acid oligomers and co-oligomers and salts thereof. The present disclosure relates to methods of making highly fluorinated sulfinic acid oligomers and co-oligomers and salts thereof.

BACKGROUND

Fluorinated sulfinates have utility in fluoropolymer and hydrocarbon processing. Methods for the synthesis of fluorinated sulfinates and their use as intermediates have been widely reported in the literature. For example, highly fluorinated alkane sulfinates can be prepared from the corresponding perfluoroalkanehalides via a dehalogenation and sulfination reaction, as reported in C. M. Hu, F. L. Quing, and W. Y. Huang, J Org Chem, 1991, 2801-2804 and W. Y. Huang, Journal of Fluorine Chemistry, 58, 1992, 1-8. Several reagent systems have been developed for use in this reaction, such as sulfite plus an oxidant, hydroxymethane sulfinate, thiourea dioxide and sodium dithionite. The use of sodium dithionite as dehalogenating and sulfinating reagent has also been reported by W. Y. Huang, B. N. Huang and W. Wang in Acta Chim. Sinica (Engl. Ed.), 1986, 178-184, and Acta Chim. Sinica (Engl. Ed.), 1986, 68-72. The later publication discloses that the reaction with an aqueous solution of the sodium dithionite is too slow for reactions involving water-insoluble perfluoroalkyl bromides, and that cosolvents are needed to improve the mutual solubility of the various reactants and permit completion of the reaction within 30 to 35 hours. Mentioned cosolvents include acetonitrile, glycol and diethylene glycol.

In another example, F. H. Wu and B. N. Huang, Journal of Fluorine Chem, 67, 1994, 233-234 reported that if DMF, acetonitrile or alcohols are used as cosolvent, both polyfluoroalkyl iodides and polyfluoroalkyl bromides will react with sodium disulfite in neutral aqueous solution to give the corresponding sulfinates in good yield. In a similar manner, $CF_3CCl_3$ reacts with sodium disulfite to give the corresponding sodium sulfinate. A disadvantage of preparing fluorinated sulfinates starting from the corresponding fluorinated iodide or bromide is that the resulting reaction product contains a large amount of by-products, particularly, inorganic salts which typically must be removed from the sulfinate.

Alternative processes for the preparation of fluorocarbon sulfinates have also been disclosed, for example, in U.S. Pat. No. 3,420,877. This particular preparation involves reacting perfluoroalkyl sulfonyl fluoride with an alkali metal sulfite or alkaline earth sulfite in an aqueous medium containing from about 10 to about 50 weight percent of a dissolved polar, inert organic solvent selected from the group consisting of dioxane, dimethoxyethane, di-n-butyl ether, tetrahydrofuran, and diethylene glycol diethyl ether. This process generally does not result in large amounts of salts that need to be removed from the resultant product, but requires use of a cosolvent that may be toxic and may have a negative impact on processes in which the sulfinate is ultimately employed, e.g., free-radical polymerization reactions. Reduction of these fluorinated sulfonyl fluorides using $NH_2NH_2$ are also known to make the corresponding sulfinates. However, all known processes are limited to making mono-sulfinates and di-sulfinates.

There continues to be a need for a process for highly fluorinated sulfinic acid oligomers and co-oligomers and salts thereof and methods of preparing them that do not require the use of toxic solvents and preferably does not require further processing or purification of the resulting reaction mixture. It is further desirable to have a favorable yield of the highly fluorinated sulfinic acid oligomers and co-oligomers and salts thereof.

SUMMARY

In one aspect, there is provided an oligomer comprising a highly fluorinated sulfinate oligomer according to the following formula (IV),

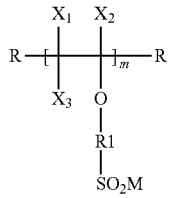

wherein $X_1$, $X_2$, and $X_3$ are independently selected from F, Cl and $CF_3$; R is independently selected from H, I, Br, linear or branched alkyl, and linear or branched fluoroalkyl group optionally containing catenary heteroatoms; R1 is a linear or branched perfluorinated linking group, which may be saturated or unsaturated, substituted or unsubstituted, and optionally comprises catenary heteroatoms; Y is a halide; M is a cation; and m is at least 2.

In another aspect, there is provided the previously disclosed oligomer further comprising a highly fluorinated vinyl ether to provide a structure according to formula (II):

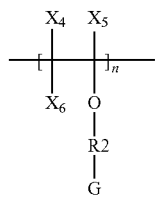

wherein $X_4$, $X_5$, or $X_6$ are independently selected from H, F, Cl and $CF_3$; R2 is a linear or branched fluorinated linking group, which may be saturated or unsaturated and substituted or unsubstituted, and optionally comprises catenary heteroatoms; G is selected from a perfluoroalkyl, a perfluoroalkoxy, a functional group, and combinations thereof; n is at least 1; and wherein $X_4$, $X_5$, $X_6$, G and R2 are selected such that the highly fluorinated vinyl ether according to formula (II) is different than the highly fluorinated oligomeric sulfonyl halide according to formula (I).

In still another aspect, there is provided the previously disclosed oligomer further comprising, in combination with formula (I) and/or highly fluorinated vinyl ether according to formula (II), an ethylenically-unsaturated monomer to provide a structure according to formula (III):

wherein Z is derived from monomers selected from ethylene, propylene, tetrafluoroethylene, chlorotrifluoroethylene, hexafluoropropylene, vinylidene fluoride, vinyl fluoride, fluorinated alkyl vinyl ethers, fluorinated alkoxy vinyl ethers, fluorinated vinyl ethers containing a functional group, perfluoro-1,3-dioxoles, and combinations thereof, and further wherein p is at least 1.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term:

"a", "an", and "the" are used interchangeably and mean one or more; and "and/or" is used to indicate one or both stated cases may occur, for example A and/or B includes, (A and B) and (A or B). Also herein, recitation of ranges by endpoints includes all numbers subsumed within that range (e.g., 1 to 10 includes 1.4, 1.9, 2.33, 5.75, 9.98, etc.). Also herein, recitation of "at least one" includes all numbers of one and greater (e.g., at least 2, at least 4, at least 6, at least 8, at least 10, at least 25, at least 50, at least 100, etc.).

"Oligomer" means less than 20,000 g/mol, less than 15,000 g/mol, less than 10,000 g/mol, less than 5,000 g/mol, less than 2,000 g/mol, less than 1,000 g/mol, and even less than 500 g/mol.

"Linking group" means a divalent linking group. In one embodiment, the linking group includes at least 1 carbon atom (in some embodiments, at least 2, 4, 8, 10, or even 20 carbon atoms). The linking group can be a linear or branched, cyclic or acyclic structure, that may be saturated or unsaturated, substituted or unsubstituted, and optionally contains one or more hetero-atoms selected from the group consisting of sulfur, oxygen, and nitrogen, and/or optionally contains one or more functional groups selected from the group consisting of ester, amide, sulfonamide, carbonyl, carbonate, urethane, urea, and carbamate.

"Highly fluorinated" means repeating monomer units that are perfluorinated with partially fluorinated end groups which may optionally contain chlorine on oligomers derived therefrom. For example, when a perfluorinated initiator is used, a perfluorinated sulfinic acid oligomer is produced. In another example, when an organic initiator is used, hydrogen atoms will be present in the "R" end groups of formula (I) (shown above).

"Sulfinate" is used to indicate both sulfinic acids and sulfinic acid salts. Also herein, "fluorosulfinate" and "fluorinated sulfinate" are used interchangeably to indicate sulfinic acids and sulfinic acid salts which contain at least one fluorine atom.

Fluoroolefins are useful as comonomers for making fluoropolymers. Fluorosulfinates are useful for producing fluoropolymers without ionic ends that benefit the processing of the polymers. A fluorosulfinic reactive monomer can be used as a surfactant, initiator and reactive monomer giving unique branched fluoropolymers. Oligomers containing fluorosulfinic acid group can initiate chain growth to provide complex fluoropolymer structures, such as, for example, a comb fluoropolymer structure.

The present disclosure relates to highly fluorinated oligomeric sulfinic acids according to formula (IV) below and salts thereof. The present disclosure relates to a method for preparing highly fluorinated oligomeric sulfinic acids. In some embodiments, the method for preparing highly fluorinated oligomeric sulfinic acids includes the steps of:

(a) providing a highly fluorinated vinyl sulfonyl halide;

(b) oligomerizing the highly fluorinated vinyl sulfonyl halide with an initiator to provide a highly fluorinated oligomeric sulfonyl halide according to the following formula (I):

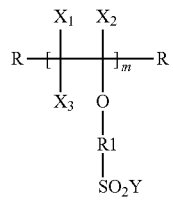

(c) and, reducing the highly fluorinated oligomeric sulfonyl halide to a highly fluorinated sulfinate oligomer according to the following formula (IV),

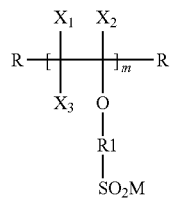

Y is a halide; M is a cation; and m is at least 2.

In some embodiments, $X_1$, $X_2$, and $X_3$ are independently selected from F, Cl and $CF_3$. R is independently selected from hydrogen, iodine, bromine, linear or branched alkyl, and linear or branched fluoroalkyl group optionally containing caternary heteroatoms. In some embodiments, the alkyl group has up to 20 carbon atoms. In some embodiments, R1 is a linear or branched perfluorinated linking group. This linking group may be saturated or unsaturated, substituted or unsubstituted, and optionally comprises catenary heteroatoms.

In some embodiments, Y is a halide. Halides useful in the present disclosure include fluorine and chlorine. M is a cation. Exemplary cations useful in the present disclosure include $H^+$, $NH_4^+$, $PH_4^+$, $H_3O^+$, $Na^+$, $Li^+$, $Cs^+$, $Ca^{+2}$, $K^+$, $Mg^{+2}$, $Zn^{+2}$, and $Cu^{+2}$, and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, $((CH_3CH_2CH_2CH_2)_4)P^+$, and the like, and combinations thereof. For methods useful in the present disclosure, m is selected from any number of 2 or higher.

In some embodiments, the highly fluorinated vinyl sulfonyl halide is a perfluorovinyl sulfonyl halide, such as, for example, a perfluorovinyl ether sulfonyl fluoride. Exemplary perfluorovinyl ether sulfonyl fluorides according to the present disclosure include, but are limited to,

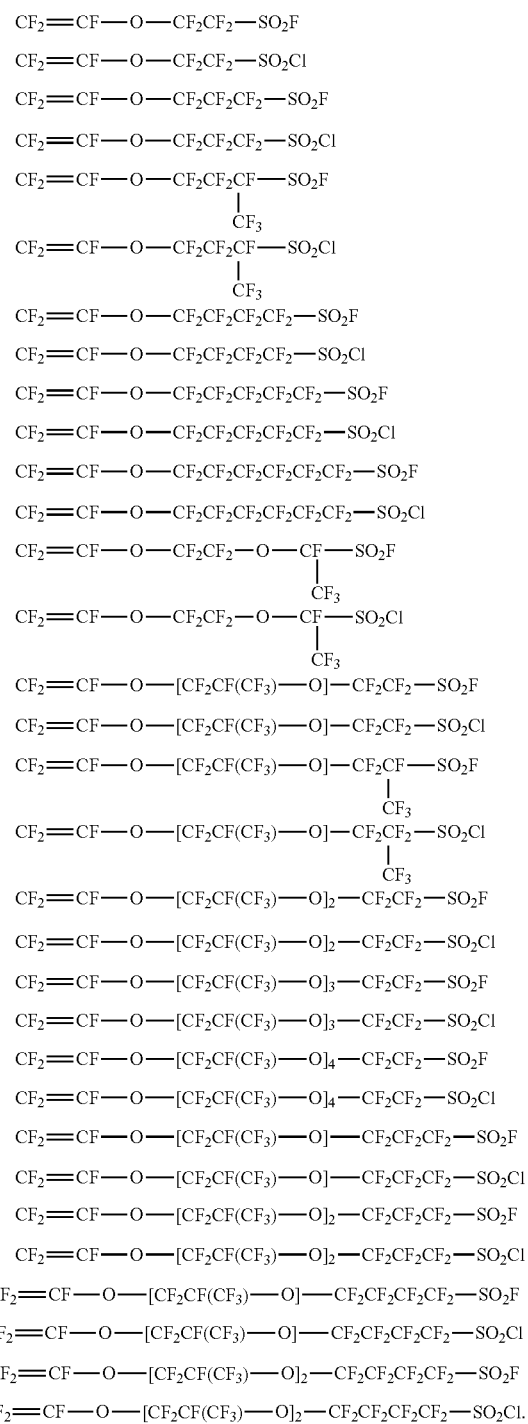

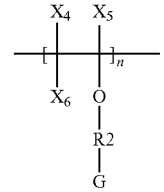

In some embodiments, the method for preparing highly fluorinated oligomeric sulfinic acids also includes step (d) acidifying the highly fluorinated sulfinate oligomer from step (c) and extracting a highly fluorinated sulfinic acid oligomer therefrom. Any acid can be used in step (d). Exemplary acids include sulfuric acid, hydrochloric acid and other strong mineral acids, and the like, and combinations thereof. Extraction can be conducted using any known extraction techniques, such as for example, using vacuum stripping and/or filtration with or without addition of an additional component. Exemplary components include, but are not limited to, an alcohol, an ether, and the like. In some embodiments, methanol is a preferred. In some embodiments methyl-t-butyl ether is preferred.

In some embodiments, the method for preparing the highly fluorinated oligomeric sulfinic acids also includes step (e) converting the highly fluorinated sulfinic acid oligomer from step (d) to form a salt thereof. In some embodiments, step (e) is conducted using an organic base. In some embodiments, step (e) is conducted using an inorganic base. In some embodiments, ammonium hydroxide is preferred. In some embodiments, potassium hydroxide is preferred.

In some embodiments, the method for preparing highly fluorinated oligomeric sulfinic acids also includes sulfonate that is produced by partial reduction of the highly fluorinated oligomeric sulfonyl halide following hydrolysis of remaining sulfonyl halide to sulfonate.

In some embodiments, the method for preparing highly fluorinated sulfinic acids also includes co-oligomerization of the highly fluorinated oligomeric sulfonyl halide according to formula (I) with a highly fluorinated vinyl ether to provide a structure according to formula (II):

In some embodiments, $X_4$, $X_5$, or $X_6$ are independently selected from H, F, Cl and $CF_3$. In some embodiments, R2 is a linear or branched fluorinated linking group. The linking group may be saturated or unsaturated and substituted or unsubstituted, and optionally comprises catenary heteroatoms.

G is selected from a perfluoroalkyl, a perfluoroalkoxy, a functional group, and combinations thereof. In some embodiments, the perfluoroalkyl group has up to 30 carbon atoms. In some embodiments, the perfluoroalkoxy group has up to 30 carbon atoms. In some embodiments, when G is a functional group, the functional group is selected from carboxylic acids and derivatives thereof, nitriles, sulfonyl halides, sulphonates, imidates, amidines, alcohols, mercaptans, iodine, bromine, and the like, and combinations thereof.

The variable n is at least 1. For methods useful in the present disclosure, $X_4$, $X_5$, $X_6$, G and R2 are selected such that the highly fluorinated vinyl ether according to formula (II) is different than the highly fluorinated oligomeric sulfonyl halide according to formula (I).

In some embodiments, the highly fluorinated vinyl ether according to formula (II) is reduced, such as for example in step (c), to produce an alcohol derivative of the highly fluorinated vinyl ether. For example, when the G in formula (II) is selected to be a carbonyl group, the highly fluorinated vinyl ether according to formula (II) is reduced in step (c) to produce an alcohol derivative thereof.

R1 in formula (I) and R2 in formula (II) are linear or branched fluorinated linking groups. In some embodiments, R1 and R2 are independently selected from $-(CF_2)_a-$, $-O(CF_2)_a-$, $-(CF_2)_a-O-(CF_2)_b-$, $-(CF_2)_a-[O-(CF_2)_b]_c-$, and $-[(CF_2)_a-O-]_b-[(CF_2)_c-O-]_d$, $-(CF_2)_a-[O-(CF(CF_3)CF_2)_b]_c$, and combinations thereof, where a, b, c, and d are independently at least 1. Exemplary linear and branched linking groups that are useful as R1 and R2 in the present disclosure include, but are not limited to, —CF$_2$CF$_2$—, —CF$_2$CF$_2$CF$_2$CF$_2$—, —CF$_2$CF(CF$_3$)—O—CF$_2$CF$_2$—.

In some embodiments, the method for preparing highly fluorinated sulfinic acids may also include, in step (b) shown above, co-oligomerization of the highly fluorinated vinyl sulfonyl halide according to formula (I) with an ethylenically-unsaturated monomer to provide a structure according to formula (III):

$$-\!\!\left(\!Z\!\right)_{\!p}\!\!-$$

In some embodiments, Z is derived from monomers selected from ethylene, propylene, tetrafluoroethylene, chlorotrifluoroethylene, hexafluoropropylene, vinylidene fluoride, vinyl fluoride, fluorinated alkyl vinyl ethers, fluorinated alkoxy vinyl ethers, fluorinated vinyl ethers containing a functional group, perfluoro-1,3-dioxoles, and the like, and combinations thereof. The variable p is at least 1.

In some embodiments, the ethylenically-unsaturated monomer according to formula (III) can be co-oligomerized with the highly fluorinated vinyl sulfonyl halide according to formula (I) and the highly fluorinated vinyl ether according to formula (II).

In some embodiments, when Z is an ethylenically-unsaturated monomer containing a functional group, the functional group is selected from bromine and/or iodine. Exemplary ethylenically-unsaturated monomers containing a functional group are derived from one or more compounds of the following formula (V):

CX$_2$=CX(Z)

In some embodiments, each X is independently selected from hydrogen or fluorine. In some embodiments, Z is selected from iodine, bromine or R$_f$—U where U is selected from iodine or bromine, and R$_f$ is a perfluorinated or partially perfluorinated alkylene group optionally containing oxygen atoms. In some embodiments, non-fluorinated bromo- or iodo-olefins, e.g., vinyl iodide and allyl iodide, can be used. Exemplary ethylenically-unsaturated monomer containing a functional group include, but are not limited to:

CH$_2$=CHI

CF$_2$=CHI

CF$_2$=CFI

CH$_2$=CHCH$_2$I

CF$_2$=CFCF$_2$I

CH$_2$=CHCF$_2$CF$_2$I

CH$_2$=CHCF$_2$CF$_2$CH$_2$CH$_2$I

CH$_2$=CH(CF$_2$)$_4$I

CH$_2$=CH(CF$_2$)$_4$CH$_2$CH$_2$I

CH$_2$=CH(CF$_2$)$_6$I

CH$_2$=CH(CF$_2$)$_6$CH$_2$CH$_2$I

CF$_2$=CFCH$_2$CH$_2$I

CF$_2$=CFCF$_2$CF$_2$I

CF$_2$=CFOCF$_2$CF$_2$I

CF$_2$=CFOCF$_2$CF$_2$CH$_2$CH$_2$I

CF$_2$=CFOCF$_2$CF$_2$CF$_2$I

CF$_2$=CFOCF$_2$CF$_2$CF$_2$CF$_2$I

CF$_2$=CFOCF$_2$CF$_2$CF$_2$CH$_2$CH$_2$I

CF$_2$=CFOCF$_2$CF$_2$CH$_2$I

CF$_2$=CFOCF$_2$CF$_2$CF$_2$CH$_2$I

CF$_2$=CFCF$_2$OCH$_2$CH$_2$I

CF$_2$=CFO(CF$_2$)$_3$OCF$_2$CF$_2$I

CH$_2$=CHBr

CF$_2$=CHBr

CF$_2$=CFBr

CH$_2$=CHCH$_2$Br

CF$_2$=CFCF$_2$Br

CH$_2$=CHCF$_2$CF$_2$Br

CF$_2$=CFOCF$_2$CF$_2$Br

CF$_2$=CFCl

CF$_2$=CFCF$_2$Cl and combinations thereof.

In some embodiments, the oligomerization step (b) is conducted in the absence of a solvent. That is, a solvent is not added to the mixture being oligomerized or co-oligomerized in step (b). In some embodiments, the oligomerization step (b) is conducted in the presence of a solvent. Solvents useful in the present disclosure include perfluorocarbons, perfluoroethers, chlorofluoroethers, chlorocarbons, hydrofluoroethers and water, and the like, and combinations thereof.

The solvent should be present in an amount sufficient to allow adequate stirring and heat transfer during the reaction. In some embodiments, the solvent can be removed after completion of the reaction.

Any conventional method may be used to remove the solvent, such as extraction, distillation under reduced pressure, column chromatography, and any other separation method.

In some embodiments, an initiator is used. Any conventional initiator can be used, such as, for example, persulfates, peroxides (e.g., organic peroxides, such as diacyl peroxides, peroxyesters, dialkyl peroxides, hyrdoperoxides, etc.), photo irradiation, gamma irradiation, azo compounds, and the like. In some embodiment, the preferred iniator is selected from peroxidic compounds. Hydrogen peroxide, acyl peroxides such as, for example, diacetyl peroxide, dipropionyl peroxide, dibutyryl peroxide, dibenzoyl peroxide, benzoyl acetyl peroxide, dilauroyl peroxide, disuccinic peroxide or diglutaric peroxide may be mentioned here, but only as examples. In addition, water-soluble peracids, such as peracetic acid, and their water-soluble salts (in particular the ammonium, sodium or potassium salts) or their esters, such as, for example, tert.-butyl peroxyacetate and tert.-butyl peroxypivalate, may be mentioned. The water-soluble salts, in particular the ammonium, potassium and sodium salts of other peracids, such as peroxomono- and peroxodisulfates, perphosphates, perborates and percarbonates may also be employed. Perfluoroacyl peroxides or Ω-hydroperfluoroacyl peroxides are furthermore suitable. Azo compounds useful in the present disclosure include azoisobutyronitrile and azo-2-cyanovaleric acid and the like. In some embodiments, certain water-soluble azo compounds are preferred. Conventional active redox systems that generate radicals to an adequate extent at temperatures between 10° C. and 50° C. can also be employed as initiators, above all in the low temperature range. An exemplary redox systems includes the combination of water-soluble peroxidic compounds, preferably peroxodisulfates, with hydrogen sulfite or with disulfite or its addition products with formaldehyde, with thiosulfate and with diimine-liberating compounds, such as, for example, with hydrazine or azodicarboxamide may be mentioned, but only as example. The salts, preferably the alkali metal salts and, in particular, the ammonium salts, of the compounds mentioned are also present in the redox combinations. If the oligomerization takes place in an organic solvent, in each case those of the abovementioned catalysts must be selected such that they are adequately soluble in the solvent concerned.

In this process, the entire amount of initiator can be added at the beginning of the oligomerization reaction in step (b). However, it may be expedient in relatively large batches to add initiator continuously during the course of the oligomerization in step (b). Equally, part of the amount of the initiator can alternatively be added at the beginning and the remainder in one or more batches can be added later. The addition of coactivators, i.e. for example, soluble salts of iron and of silver, may be advantageous, in particular when redox systems are used as initiators.

Reducing agents useful in the present disclosure include those commonly known as reducing agents, such as, for example, those listed below. Exemplary reducing agents include metal hydrides, such as $MeLH_4$, where Me is an alkaline metal and L is either an aluminum or a boron and $MeH_x$, where Me is either an alkaline metal or an alkaline earth metal, and x is 1 or 2. These types of reducing agents include, for example, lithium aluminum hydride, lithium boron hydride, potassium boron hydride, sodium boron hydride, sodium hydride, lithium hydride, potassium hydride, barium hydride, calcium hydride, and the like. In some embodiments, the preferred reducing agent is sodium borohydride.

In some embodiments, useful reducing agents include reductive inorganic acids. These types of reducing agents include, for example, hydracid iodide, hydracid bromide, hydrophosphoric acid, hydracid sulfide, arsenious acid, phosphorous acid, sulfurous acid, nitrous acid, formic acid, oxalic acid, and the like. In some embodiments, useful reducing agents include mixtures of metals and acids. Metals useful in these types of reducing agents include, for example, tin, iron, zinc, amalgam of zinc, and the like. Acids useful in these types of reducing agents include, for example, hydrochloric acid, sulfuric acid, acetic acid, phosphoric acid, formic acid, trifluoromethane sulfonic acid, trifluoroacetic acid, trichloroacetic acid, and the like.

In some embodiments, useful reducing agents include organic metal compounds, such as, for example, butyl lithium, Grignard reagent (such as alkyl carbon atom of 1 to 8), aryl magnesium halide, triethyl aluminum, trisobutyl aluminum, sodium-benzene, sodium-naphthalene, and the like. In some embodiments, metal compounds with low valences are useful reducing agents, such as, for example, stannous chloride, ferrous sulfate, titanium trichloride, ferrous chloride, stannous sulfate, ferrous sulfide, stannous sulfide, ferrous bromide, stannous bromide, ferrous hydroxide, and the like. In some embodiments, reductive salts of inorganic acids and compounds of the same are useful reducing agents. These types of reducing agents include, for example, iodides, bromides, sulfides, phosphites, sulfites, arsenites, dithionites, nitrites, formates, and the like. Mixtures of metals, water, steam, alcohols or alkalis can also be used as reducing agents in the present disclosure. Also useful as reducing agents are reductive organic compounds, such as, for example, triethanolamine, acetaldehyde, formaldehyde, propyl aldehyde, and the like, and reductive gases, such as, for example, carbon monoxide, sulfur dioxide, hydrogen iodide, hydrogen bromide, hydrogen sulfide, and the like. In some embodiments, a reducing agent useful in the present disclosure is selected from at least one of sodium borohydride, potassium borohydride, lithium aluminum hydride, $NH_2NH_2$, $K_2SO_3$, $Na_2SO_3$, $NaHSO_3$ and $KHSO_3$.

The following embodiments are representatives of the subject matter of the present application:

Embodiment 1. An oligomer comprising a highly fluorinated sulfinate oligomer according to the following formula (IV),

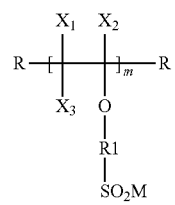

wherein $X_1$, $X_2$, and $X_3$ are independently selected from F, Cl and $CF_3$; R is independently selected from H, I, Br, linear or branched alkyl, and linear or branched fluoroalkyl group optionally containing catenary heteroatom; R1 is a linear or branched perfluorinated linking group, which may be saturated or unsaturated, substituted or unsubstituted, and optionally comprises catenary heteroatoms; Y is a halide; M is a cation; and wherein m is at least 2.

Embodiment 2. The oligomer of embodiment 1 further comprising salts derived from the highly fluorinated sulfinate oligomer according to the following formula (IV).

Embodiment 3. The oligomer of embodiments 1 or 2 further comprising a second unit according to formula (II):

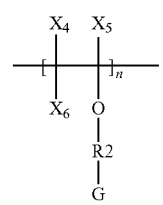

wherein $X_4$, $X_5$, or $X_6$ independently selected from H, F, Cl and $CF_3$; R2 is a linear or branched fluorinated linking group, which may be saturated or unsaturated and substituted or unsubstituted, and optionally comprises catenary heteroatoms; G is selected from a perfluoroalkyl and a functional group; n is at least 1; and wherein $X_4$, $X_5$, $X_6$, G and R2 are selected such that a resulting unit according to formula (II) is different than a resulting unit according to formula (I).

Embodiment 4. The oligomer according to embodiment 3 wherein the functional group is selected from carboxylic acids and derivatives thereof, nitriles, sulfonyl halides, sulphonates, imidates, amidines, mercaptans, alcohols, iodine, bromine, and combinations thereof.

Embodiment 5. The oligomer of embodiments 3 or 4 wherein the functionalized perfluorovinyl ether according to formula (II) wherein when the functional group is a carbonyl group, the functional group is reduced to provide an alcohol derivative.

Embodiment 6. The oligomer of embodiment 1 further comprising an ethylenically-unsaturated monomer to provide a structure according to formula (III):

wherein Z is derived from monomers selected from ethylene, propylene, tetrafluoroethylene, chlorotrifluoroethylene, hexafluoropropylene, vinylidene fluoride, vinyl fluoride, fluorinated alkyl vinyl ethers, fluorinated alkoxy vinyl ethers, fluorinated vinyl containing a functional group, perfluoro-1,3-dioxoles, and combinations thereof, and further wherein p is at least one.

Embodiment 7. The oligomer of embodiment 3 further comprising an ethylenically-unsaturated monomer to provide a structure according to formula (III):

wherein Z is derived from monomers selected from ethylene, propylene, tetrafluoroethylene, chlorotrifluoroethylene, hexafluoropropylene, vinylidene fluoride, vinyl fluoride, fluorinated alkyl vinyl ethers, fluorinated alkoxy vinyl ethers, fluorinated vinyl containing a functional group, perfluoro-1,3-dioxoles, and combinations thereof, and further wherein p is at least one.

Embodiment 8. The oligomer according to any of the preceding embodiments wherein R1 and R2 are independently selected from: $—(CF_2)_a—$, $—O(CF_2)_a—$, $—(CF_2)_a—O—(CF_2)_b—$, $—(CF_2)_a—[O—(CF_2)_b]_c—$, $—(CF_2)_a—[O—(CF(CF_3)CF_2)_b]_c—$, and $—[(CF_2)_a—O—]_b—[(CF_2)_c—O—]_d—$, and combinations thereof, wherein a, b, c, and d are independently at least 1.

Embodiment 9. The oligomers according to any of the preceding embodiments, wherein R1 and R2 are independently selected from: $—CF_2CF_2—$, $—CF_2CF_2OCF_2CF_2—$, $—CF_2CF(CF_3)—O—CF_2CF_2—$.

Embodiment 10. The oligomer according to any of the preceding embodiments wherein the oligomers has a number average molecular weight of no more than 20,000 grams/mole.

Embodiment 11. The composition according to any one of the preceding embodiments, wherein M is selected from: $H^+$, $NH_4^+$, $PH_4^+$, $H_3O^+$, $Na^+$, $Li^+$, $Cs^+$, $Ca^{+2}$, $K^+$, $Mg^{+2}$, $Zn^{+2}$, and $Cu^{+2}$, and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, $((CH_3CH_2CH_2CH_2)_4)P^+$, and combinations thereof.

Embodiment 12. The oligomers according to any one of the preceding embodiments, wherein the oligomer is water soluble.

Embodiment 13. An aqueous emulsion comprising the oligomer of any of the preceding embodiments.

Embodiment 14. A fluoropolymer derived from the aqueous emulsion of embodiment 13.

EXAMPLES

The following examples are merely for illustrative purposes and are not meant to limit in any way the scope of the appended claims. All parts, percentages, ratios, and the like in the examples are by weight, unless noted otherwise. All materials used herein were obtained from Sigma-Aldrich Chemical Company; Milwaukee, Wis. unless otherwise noted.

Materials

| Material | Source |
|---|---|
| MV4S | $CF_2=CF—O—C_4F_8—SO_2F$, made as described in the Example (section A to C) of U.S. Pat. No. 6,624,328 (Guerra) |
| LUPEROX 575 | t-amyl-2-ethyl hexanoate peroxide, commercially available from Arkema, Philadelphia, PA |
| LUPEROX TAEC | t-amyl peroxy 2-ethylhexyl carbonate, commercially available from Arkema, Philadelphia, PA |
| VAZO 67 | EtMeC(CN)—N=N—CEtMeCN commercially available from DuPont, Wilmington, Delaware |
| CTFE-Dimer | $ClCFClCF_2CFClCF_2Cl$ and commercially available from Halocarbon Products Corp., River Edge, NJ |
| VDF | Vinylidene fluoride, commercially available from Sigma-Aldrich Chemical Company; Milwaukee, Wisconsin |
| MV5CO2CH3 | $CF_2=CF—O—C_5F_{10}—CO_2CH_3$ made as per Example 9 below |
| MV31 | $CF_2=CF—O—C_3F_6—O—CF_3$ made as per Example 8 of U.S. Pat. No. 6,255,536 (Worm et al.) |
| MV3b2S | $CF_2=CF—O—CF_2CF(CF_3)—OC_2F_4—SO_2F$, Perfluoro(4-methyl-3,6-dioxaoct-7-ene)sulfonyl fluoride available from SynQuest Lab, Alachua FL. |
| o-MV4S | $R—[CF_2CF(OC_4F_8SO_2F)]n-R$ where n = 2-25 and R can be $C_4F_9$, $CF_3OCF_2CF_2$, I, H, COOH, $C_2H_5$ and/or $C_7H_{15}$ |
| o-MV4SO2H | $R—[CF_2CF(OC_4F_8SO_2H)]n-R$ where n = 2-5 and R can be $C_4F_9$, I, H, $C_2H_5$ and/or $C_7H_{15}$ |
| o-MV4SO2NH4 | $R—[CF_2CF(OC_4F_8SO_2NH_4)]n-R$ where n = 2-5 and R can be $C_4F_9$, I, H, $C_2H_5$ and/or $C_7H_{15}$ |
| o-MV3b2S | $R—[CF_2CF(OCF_2CF(CF_3)OC_2F_4SO_2F)]n-R$ where n = 2-5 and R can be H, $C_2H_5$ and/or $C_7H_{15}$ |
| o-MV3b2SO2H | $R—[CF_2CF(OCF_2CF(CF_3)OC_2F_4SO_2H)]n-R$ where n = 2-5 and R can be H, $C_2H_5$ and/or $C_7H_{15}$ |
| o-MV3b2SO2NH4 | $R—[CF_2CF(OCF_2CF(CF_3)OC_2F_4SO_2NH_4)]n-R$ where n = 2-5 and R can be H, $C_2H_5$ and/or $C_7H_{15}$ |

Example 1

200 grams (0.53 mol) of MV4S and 20 grams (0.09 mol) of "LUPEROX 575" were charged to an evacuated 600 ml reactor, such as the reactor commercially available under the trade designation "600 ml SERIES 4520 PARR" from Parr Instruments, Moline, Ill. ("600 ml PARR reactor"). The mixture was stirred and heated to 65° C. for 20 hours. A slight pressure rise was measured and vented after the reaction reached 20° C. A product mixture of 217 grams was drained and fractionated to give 97 grams of unreacted MV4S and 106 grams of oligomerized MV4S (o-MV4S) for a 53% yield. A 38 gram sample of the o-MV4S was heated under vacuum to remove a cut boiling at 145° C. and 4.6 mm. The higher boiling product of 28.4 grams remained in the pot. The 28.4 grams of higher boiling material was subjected to Liquid Chromatography-Mass Spectroscopy (LCMS) and relative areas indicated the general structure R—$[CF_2CF(OC_4F_8SO_2F]_n$—R where n equaled 2 to 5 and R was H, $C_2H_5$ and/or $C_7H_{15}$. The average oligomer had 2.9 units and an average molecular weight of 1200 grams per mole.

Example 2

6.3 grams (0.17 mol) of sodium borohydride in 100 grams of tetrahydrorfuran (THF) was charged to a 500 ml 3-neck round bottom flask and stirred. 25 grams (0.06 mol) of o-MV4S made in Example 1 (having an average of 2.9 oligomer units) was dissolved in 50 grams of THF and added over 15 minutes. A slight exothermic reaction occurred upon addition of the o-MV4S solution. The mixture was allowed to react at 65° C. for two hours. Solvent was vacuum stripped and 14 grams of concentrated sulfuric acid in 200 grams of water was added at 20° C. This mixture was vacuum stripped and the resulting solids were extracted with 100 grams of methanol. The extracted mixture was then filtered and vacuum stripped again to give 26.5 grams of tacky solid product that was then diluted to 50 grams with water. Nuclear magnetic resonance spectroscopy (NMR) gave the desired o-MV4SO$_2$H for a 98% yield.

Example 3

200 grams (0.53 mol) of MV4S, 27 grams (0.12 mol) of "LUPEROX 575" and 52 grams of CTFE-Dimer were placed in an evacuated 600 ml PARR reactor and the mixture was stirred and heated to 65° C. for 20 hours. A slight pressure rise was measured and vented after the reaction was at 20° C. A product mixture of 268 grams was drained and fractionated to give 50 grams of o-MV4S having a boiling point greater than 225° C. at 15 mm vacuum. Relative area percents from LCMS showed oligomers with the general structure of R—$[CF_2CF(OC_4F_8SO_2F)]_n$—R where n equaled 2 to 5 and R was one of H, $C_2H_5$ and/or $C_7H_{15}$. The average oligomer had 3.2 units and an average molecular weight of 1320 grams per mole under this reaction condition and work up.

Example 4

In a 1 liter 3-neck round bottom flask were added 40 grams (0.11 mol) of o-MV4S product from Example 3 in 100 grams of THF to a stirred solution of 9 grams (0.24 mol) of sodium borohydride in 100 grams of THF. A slight exothermic reaction occurred within 10 minutes of adding the o-MV4S solution. The reaction was allowed to run at 65° C. for 20 hours. 25 grams of concentrated sulfuric acid in 200 grams of water was added at 20° C. A top product phase of 135 grams of product with THF was vacuum stripped. A 50 gram methanol charge was used to dissolve the product and this was filtered and vacuum stripped to give 35 grams of o-MV4SO2H. NMR showed the presence of the desired o-MV4SO2H.

Example 5

The ammonium salt was made by adding 35 grams of o-MV4SO2H made in Example 4 to 6.1 grams (0.1 mol) of ammonia as 27% ammonium hydroxide and vacuum stripping to give 38 grams of o-MV4SO2NH4 salt as a tacky solid. No melting point was found and at 209° C. onset of decomposition was measured for o-MV4SO2NH4.

Example 6

In a 100 ml bottle was charged 26 grams (0.07 mol) of MV4S, 50 grams of distilled water, 1 gram (0.0004 mol) of 50% solution of o-MV4SO2NH4 made in Example 5, 0.3 grams (0.001 mol) of sodium persulfate and 0.6 grams (0.003 mol) of potassium phosphate. The solution was nitrogen purged and placed in a launder-ometer, such as the device commercially available under the trade designation "Launder-Ometer M228AA" from SDL Atlas, Rock Hill, South Caroline, for 20 hours at 80° C. 15 grams of unreacted MV4S was recovered as a lower phase. The remaining solution was freeze thawed to precipitate 5 grams of viscous cold flowing polymer that was subjected to LCMS and found to have a molecular weight that was too high for detection by this method. $^{19}$F NMR showed presence of the desired o-MV4S having the general structure R—$[CF_2CF(OC_4F_8SO_2F]$n-R where n equaled an average number of 25 and R was COOH and H. The average oligomer had an average molecular weight of 9,600 grams per mole under this reaction condition and work up.

Example 7

100 grams (0.26 mol) of MV4S, 17 grams (0.07 mol) of "LUPEROX 575" and 103 grams of CTFE-Dimer were charged to an evacuated 600 ml PARR reactor. The mixture was stirred and 17 grams (0.27 mol) of vinylidene fluoride was charged. The resulting mixture was heated to 65° C. for 20 hours. A slight pressure rise was measured and vented after the reaction was at 20° C. A product mixture of 207 grams was drained and fractionated to give 57 grams of co-oligomeric o-MV4S/VDF having a 50% yield based on input monomers with a boiling point greater than 75° C. at 15 mm vacuum. Relative area percents from LCMS showed co-oligomers with the general structure of R4CF$_2$CF(OC$_4$F$_8$SO$_2$F)x-[CH$_2$CF$_2$]y-R where x and y equaled 2 to 5 and R was one of H, $C_2H_5$ and/or $C_7H_{15}$. The average co-oligomer had 3.1 units and an average molecular weight of 1478 grams per mole under this reaction condition and work up.

Example 8

100 grams (0.26 mol) of MV4S, 15 grams (0.04 mol) of $C_4F_9I$, 10 grams (0.04 mol) of "LUPEROX 575" and 25 grams of CTFE-Dimer were charged to an evacuated 600 ml PARR reactor. The mixture was stirred and heated to 65° C. for 20 hours. A slight pressure rise was measured and vented after the reaction reached 20° C. A product mixture of 145 grams was drained and fractionated to give 9 grams of oligomeric o-MV4S with a boiling point greater than 180° C. at 15 mm vacuum. Relative area percents from LCMS showed oligomers with the general structure of R—[CF$_2$CF $(OC_4F_8SO_2F)]n$-R where n equaled 2 to 5 and R was one of $C_4F_9$, I, H, $C_2H_5$ and/or $C_7H_{15}$. The average oligomer had 3.2 units and an average molecular weight of 1350 grams per mole under this reaction condition and work up.

Example 9

6.1 grams of KF (0.1 mol), 390 grams of diglyme were charged in a 600 ml PARR reactor and cooled to −5° C. with stirring. 170 grams of perfluoroadipoyl fluoride (0.87 mol) (available from Exfluor Research in Austin, Tex.) was charged to the reactor followed by 140 grams (0.85 mol) of hexafluoropropylene oxide (available from E. I. du Pont de Nemours and Company, Wilmington, Del.) and the reaction proceeded for over one hour. The reaction was heated to 25° C. and 250 grams of product $FCOC_5F_{10}$—O—$CF(CF_3)COF$ distilled over at 135° C. A 2-liter 3-neck round bottom flask was charged with 192 grams (1.8 mol) of $Na_2CO_3$, 390 grams of diglyme and stirred. 250 grams (0.69 mol) of $FCOC_5F_{10}$—O—$CF(CF_3)COF$ was slowly added and the reaction temperature heated up to 71° C. The slurry was heated up to 162° C. to decarboxylate the slurry until no more $CO_2$ was evolved. The reaction was cooled to 25° C. and 215 grams (2.19 mol) of concentrated $H_2SO_4$ in 350 grams of water was added. A top phase of 540 grams was further washed with 64 grams of concentrated $H_2SO_4$ in 200 grams of water to obtain 317 grams of a bottom phase as a crude product. The bottom phase product was esterified with 116 grams (3.63 mol) of methanol and 92 grams (0.94 mol) of concentrated $H_2SO_4$ by heating to 82° C. for 20 hours. The reaction was cooled to 25° C. and 200 grams of water was added to isolate 189 grams of the bottom phase product as the crude product. Vacuum distillation yielded 129 grams (0.32 mol) of $CF_2$=CF—O—$C_5F_{10}$—$CO_2$—$CH_3$ with a boiling point of 132° C./15 mm.

100 grams (0.26 mol) of MV4S, 20 grams (0.05 mol) of MV5CO2CH3, 10 grams (0.04 mol) of "LUPEROX 575" and 25 grams of CTFE-Dimer were charged to an evacuated 600 ml PARR reactor. The mixture was stirred and heated to 65° C. for 20 hours. A slight pressure rise was measured and vented after the reaction was at 20° C. A product mixture of 144 grams was drained and fractionated to give 24 grams of co-oligomeric o-MV4S/MV5CO$_2$CH$_3$ with a boiling point greater than 225° C. at 15 mm vacuum. Relative area percents from LCMS showed oligomers with the general structure of R—$[CF_2CF(OC_4F_8SO_2F)]x$-$[CF_2CF(OC_5F_{10}CO_2CH_3)]y$-R where x and y equaled 2 to 5 and R was one of H, $C_2H_5$ and/or $C_7H_{15}$. The average co-oligomer had 3.2 units and an average molecular weight of 1320 grams per mole under this reaction condition and work up.

Example 10

To a 250 milliliter 3-neck round bottom flask were added 18 grams (0.02 mol) of o-MV4S/MV5CO2CH3 product from Example 9 in 20 grams of THF to a stirred solution of 1.5 grams (0.04 mol) of sodium borohydride in 50 grams of THF. A slight exothermic reaction occurred with the addition within 10 minutes of adding the o-MV4S/MV5CO2CH3 solution. The reaction was allowed to run at 65° C. for 1 hour. 10 grams of concentrated sulfuric acid in 50 grams of water was added at 20° C. A 50 gram methyl-t-butyl ether charge was used to extract the product and vacuum stripped to give 17 grams of R—$[CF_2CF(OC_4F_8SO_2H)]x$-$[CF_2CF(OC_5F_{10}CH_2OH)]y$-R where x and y equaled 2 to 5 and R was one of H, $C_2H_5$ and/or $C_7H_{15}$. Nuclear magnetic resonance spectroscopy (NMR) showed the desired co-oligomer having both fluorosulfinic acid and fluoroalcohol groups with a 94% yield.

Example 11

100 grams (0.26 mol) of MV4S, 14 grams (0.04 mol) of MV31, 10 grams (0.04 mol) of "LUPEROX 575" and 25 grams of CTFE-Dimer were charged to an evacuated 600 ml PARR reactor. The mixture was stirred and heated to 65° C. for 20 hours. A slight pressure rise was measured and vented after the reaction was at 20° C. A product mixture of 146 grams was drained and fractionated to give 23 grams of co-oligomeric o-MV4S/MV31 with a boiling point greater than 225° C. at 15 mm vacuum. Relative area percents from LCMS showed oligomers with the general structure of R—$[CF_2CF(OC_4F_8SO_2F)]x$-$[CF_2CF(OC_3F_6OCF_3)]y$-R where x and y equaled 2 to 5 and R was one of H, $C_2H_5$ and/or $C_7H_{15}$. The average co-oligomer had 3.4 units and an average molecular weight of 1375 grams per mole under this reaction condition and work up.

Example 12

An evacuated 600 ml PARR reactor was charged with 50 grams (0.11 mol) of MV3b2S, 7 grams (0.03 mol) of "LUPEROX 575" and 196 grams of CTFE-Dimer. The mixture was stirred and heated to 65° C. for 20 hours. A slight pressure rise was measured and vented after the reaction was at 20° C. A product mixture of 248 grams was drained and fractionated to give 8 grams of o-MV3b2S having a boiling point greater than 225° C. at 15 mm vacuum. Relative area percents from LCMS showed oligomers with the general structure of R—$[CF_2CF(OCF_2CF(CF_3)OC_2F_4SO_2F)]n$-R where n equaled 2 to 5 and R was one of H, $C_2H_5$ and/or $C_7H_{15}$. The average oligomer had 2.5 units and an average molecular weight of 1250 grams per mole under this reaction condition and work up.

Example 13

To a 250 milliliter 3-neck round bottom flask was added 6 grams (0.01 mol) of o-MV3b2S product from example 12 in 20 grams of THF to a stirred solution of 1.5 grams (0.03 mol) of sodium borohydride in 50 grams of THF. A slight exothermic reaction occurred with the addition within 10 minutes of adding the o-MV3b2S solution. The reaction was allowed to run at 65° C. for 1 hour. 10 grams of concentrated sulfuric acid in 50 grams of water was added at 20° C. A 50 gram methyl-t-butyl ether charge was used to extract the product, which was then and vacuum stripped to give 5.3 grams of o-MV3b2SO$_2$H (91% yield). Nuclear magnetic resonance spectroscopy (NMR) confirmed the presence of the desired o-MV3b2SO$_2$H.

Example 14

The ammonium salt was made by adding 5 grams of the o-MV3b2SO2H made in example 13 to 6.1 grams (0.1 mol) of ammonia as 27% ammonium hydroxide and vacuum stripping to give 5.2 grams of o-MV3b2SO2NH4 salt as a tacky solid. The melting point was 156° C. and onset of decomposition was 183° C.

Example 15

280 g (1.2 mol) $CF_3OC_2F_4COF$ (made by electrochemical fluorination as described in example 2 of U.S. Pat. No. 2,713, 593 to Brice et al) was added to excess methanol cooled to −20° C. in a 1 L 3-neck round bottom flask. This was then water washed to isolate 295 g (1.2 mol) $CF_3OC_2F_4CO_2CH_3$ as the fluorochemical lower phase. A charge of 89 g (1.35 mol) KOH in 150 g water was then added to the previous fluorochemical to make the $CF_3OC_2F_4CO_2K$ salt. This was dried and acidified with 150 g of concentrated $H_2SO_4$ in 150 g water and vacuumed distilled to isolate 314 g (1.3 mol) of $CF_3OC_2F_4CO_2H$. 50 g (0.22 mol) $CF_3OC_2F_4CO_2H$, 4 g dimethylformamide and 30 g (0.2.5 mol) thionyl chloride were reacted in a 500 mL 3-neck round bottom flask at 72° C. for one hr followed by distillation to give 46 g (0.19 mol) $CF_3OC_2F_4COCl$. To a 250 ml 3-neck round bottom flask was added 4.7 g (0.05 mol) 35% HOOH which was then cooled to 0° C. with stirring followed by the addition of 4 g (0.1 mol) of NaOH in 90 g water. The reaction was kept at 10° C. and held for 30 min followed by addition at 10° C. of 20 g (0.08 mol) $CF_3OC_2F_4COCl$ in 180 g of "FC-72 FLUORINERT" (commercially available from 3M Company, St. Paul, Minn.). The solution was stirred at 10° C. for 30 min and the lower phase was removed containing 10 weight % $CF_3OC_2F_4COOOCOC_2F_4OCF_3$ in "FC-72 FLUORINERT" confirmed by FNMR and FTIR. 120 g (0.32 mol) MV4S was added to a 500 ml 3-neck round bottom flask with a stir bar and cooled to 0° C. This was followed by addition of 100 g of 10 weight percent (0.02 mol) $CF_3OC_2F_4COOOCOC_2F_4OCF_3$ in "FC-72 FLUORINERT" with stirring at 10° C. for 2 hrs. The solution was further reacted for 20 hrs at 25° C. The product mixture was fractionated to give 11 g of o-MV4S having a boiling point greater that 150° C. at 8 mm vacuum. FNMR confirmed the desired perfluoro o-MV4S having $CF_3OCF_2CF_2$ end groups and the general structure $CF_3OCF_2CF_2-[CF_2CF(OC_4F_8SO_2F)]_n-CF_2CF_2OCF_3$ where n was an average of 15. The oligomer had an average molecular weight of 6050 g per mole under this reaction condition and work up.

Example 16

50 grams of MV4S was oligomerized with 6.21 grams of "LUPEROX TAEC" at 120° C. under nitrogen for 24 hours. The low boiling fractions were stripped out at 120° C. under vacuum to yield 31 grams of a viscous liquid with a 62% isolated yield. FTIR showed a signal at 2968 cm$^{-1}$ for CH from the hydrocarbon initiator and strong signals at 1463, 1349, 1212, 1148 and 1072 cm$^{-1}$ for C—F and —SO$_2$F groups. $^{19}$F NMR showed no signal for a CF=CFO— group, two signals for —CF$_2$O— at −81 and −87 ppm, a SO$_2$F signal at +43 ppm, —CF$_2$SO$_2$F signal at −110 ppm, and CF$_2$CF$_2$— signals at −123 and −128. The oligomerized vinyl signals of —(CF$_2$CF(O—)— were seen at −121 and −147 ppm with complicated multiplets. From LCMS analysis the oligomer had an average of 3.2 units and an average molecular weight of 1320 grams per mole.

25.6 grams of the above viscous oligomer liquid (~0.067 eq —SO$_2$F) in 37 grams of THF solvent was treated with 0.5 grams of NaBH$_4$ (0.0132 mol) at −5 to 10° C. under nitrogen for 20 minutes followed by reaction at 20° C. for 2 additional hours. $^{19}$F NMR indicated 20% —SO$_2$F (+43 ppm) was reacted to give the corresponding —SO$_2$M, the corresponding signal of —CF$_2$SO$_2$F at −111 ppm was decreased and a new signal at −132 ppm for —CF$_2$SO$_2$M appeared. 0.28 grams of NaBH$_4$ (total 0.78 grams, 0.0206 mole) was added at −5 to 10° C. over 20 minutes followed by reaction at 20° C. for 2 hours. The conversion was increased to 36%. Repeating the addition of NaBH$_4$ a third time the conversion was increased to 50% when 1.1 grams of total NaBH$_4$ (0.029 mol) was added. $^{19}$F NMR indicated —OCF$_2$CF$_2$CF$_2$CF$_2$SO$_2$M with chemical shifts at −126, −128 and −132, and —OCF$_2$CF$_2$CF$_2$CF$_2$SO$_2$F with chemical shifts at −123, −128 and −111 ppm. The remaining signal of —SO$_2$F was seen at +42 ppm.

5 grams water was added with stirring to the above partially reduced oligomer solution in THF to destroy any unreacted reducing agent. This solution was then treated with 10% KOH aqueous solution at 20° C. while stirring until the pH of solution was basic (pH greater than 9). The solution was stirred at 20° C. for another 30 minutes. $^{19}$F NMR indicated the —SO$_2$F signal at +42 ppm had completely disappeared. After acidification of the solution with 2NH$_2$SO$_4$ to a pH of less than 2 the mixture was extracted with methyl-t-butyl ether (3×50 mL). After stripping out the solvent, 32 grams of a wet product was obtained. The wet product was dissolved in 20 grams of water. $^{19}$F NMR analysis of the solution indicated about 50 wt % solids and a mole ratio of —CF$_2$SO$_2$H (−132 ppm) and —CF$_2$SO$_3$H (−111 ppm) of 54:46.

Example 17

Similar to what was done in Example 16, 50 grams of MV4S was oligomerized with 2.81 grams of VAZO 67 (5.6 wt %) under nitrogen at 120° C. for 24 hours. Filtration to remove solids at 25° C., the filtered solution was stripped at 100° C. under full vacuum to remove low boiling point components. 9.7 grams of high viscose liquid oligomers were obtained (19% yield). $^{19}$F NMR analysis showed no more CF=CFO— signal. From LCMS analysis the oligomer had an average of 2.6 units and an average molecular weight of 1071 grams per mole.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows and multi-layer articles created by this process.

What is claimed is:

1. An oligomer comprising a highly fluorinated sulfinate oligomer according to the following formula (IV),

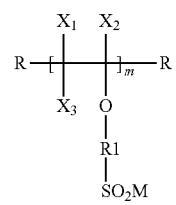

wherein $X_1$, $X_2$, and $X_3$ are independently selected from F, Cl and $CF_3$; R is independently selected from H, I, Br, linear or branched alkyl, and linear or branched fluoroalkyl group optionally comprising a heteroatom; R1 is a linear or branched perfluorinated linking group, which may be saturated or unsaturated, substituted or unsubstituted, and optionally comprising a heteroatom; M is a cation; and wherein m is at least 2, further wherein the oligomer has a molecular weight of less than 20,000 grams per mole.

2. The oligomer of claim 1 further comprising salts derived from the highly fluorinated sulfinate oligomer.

3. The oligomer of claim 1 further comprising a second unit according to formula (II):

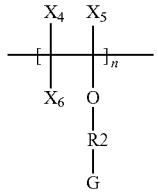

wherein $X_4$, $X_5$, or $X_6$ independently selected from H, F, Cl and $CF_3$; R2 is a linear or branched fluorinated linking group, which may be saturated or unsaturated and substituted or unsubstituted, and optionally comprising heteroatoms; G is selected from a perfluoroalkyl and a functional group; n is at least 1.

4. The oligomer according to claim 3 wherein the functional group is selected from carboxylic acids and derivatives thereof, nitriles, sulfonyl halides, sulphonates, imidates, amidines, mercaptans, alcohols, iodine, bromine, and combinations thereof.

5. The oligomer of claim 3 wherein the functional group is an alcohol derivative.

6. The oligomer of claim 1 further comprising an ethylenically-unsaturated monomer to provide a structure according to formula (III):

wherein Z is derived from monomers selected trom ethylene, propylene, tetrafluoroethylene, chlorotrifluoroethylene, hexafluoropropylene, vinylidene fluoride, vinyl fluoride, fluorinated alkyl vinyl ethers, fluorinated alkoxy vinyl ethers, fluorinated vinyl containing a functional group, perfluoro-1,3-dioxoles, and combinations thereof, and further wherein p is at least one.

7. The oligomer of claim 3 further comprising an ethylenically-unsaturated monomer to provide a structure according to formula (III):

wherein Z is derived from monomers selected trom ethylene, propylene, tetrafluoroethylene, chlorotrifluoroethylene, hexafluoropropylene, vinylidene fluoride, vinyl fluoride, fluorinated alkyl vinyl ethers, fluorinated alkoxy vinyl ethers, fluorinated vinyl containing a functional group, perfluoro-1,3-dioxoles, and combinations thereof, and further wherein p is at least one.

8. The oligomer of claim 1 or 3, wherein R1 and R2 are independently selected from: $-(CF_2)_a-$, $-O(CF_2)_a-$, $-(CF_2)_a-O-(CF_2)_b-$, $-(CF_2)_a-[O-(CF_2)_b]_c-$, $-(CF_2)_a-[O-(CF(CF_3)CF_2)_b]_c-$, and $-[(CF_2)_a-O-]_b-[(CF_2)_c-O-]_d-$, and combinations thereof, wherein a, b, c, and d are independently at least 1.

9. The oligomer of claim 1 or 3, wherein R1 and R2 are independently selected from:
$-CF_2CF_2-$, $-CF_2CF_2OCF_2CF_2-$, $-CF_2CF(CF_3)-O-CF_2CF_2-$.

10. The oligomer of claim 1 wherein the oligomers has a number average molecular weight of no more than 20,000 grams/mole.

11. The oligomer of claim 1, wherein M is selected from: $H^+$, $NH_4^+$, $PH_4^+$, $H_3O^+$, $Na^+$, $Li^+$, $Cs^+$, $Ca^{+2}$, $K^+$, $Mg^{+2}$, $Zn^{+2}$, and $Cu^{+2}$, and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, $((CH_3CH_2CH_2CH_2)_4)P^+$, and combinations thereof.

12. The oligomer of claim 1, wherein the oligomer is water soluble.

13. An aqueous emulsion comprising the oligomer of claim 1.

14. A fluoropolymer derived from the aqueous emulsion of claim 13.

* * * * *

UNITED STATES PATENT AND TRADEMARK OFFICE
CERTIFICATE OF CORRECTION

PATENT NO. : 9,266,999 B2  
APPLICATION NO. : 13/995037  
DATED : February 23, 2016  
INVENTOR(S) : Guerra et al.

Page 1 of 2

It is certified that error appears in the above-identified patent and that said Letters Patent is hereby corrected as shown below:

On the Title Page

Column 2, item (56)  
Line 2, (Other Publication), Delete "polyfluoroalky" and insert -- polyfluoroalkyl --, therefor.

In the Specification

Column 1  
Line 39, Delete "perfluoralkyl" and insert -- perfluoroalkyl --, therefor.

Column 2  
Line 35 (Approx.), Delete "caternary" and insert -- catenary --, therefor.

Column 4  
Line 46 (Approx.), Delete "caternary" and insert -- catenary --, therefor.

Column 5  
Line 33-34, Delete "—$CF_2CF_2$—," and insert -- —$CF_2CF$—, --, therefor.

Column 8  
Line 51, Delete "hyrdoperoxides," and insert -- hydroperoxides, --, therefor.  
Line 53, Delete "iniator" and insert -- initiator --, therefor.

Column 9  
Line 59, Delete "trisobutyl" and insert -- triisobutyl --, therefor.

Column 10  
Line 9 (Approx.), Delete "monooxide," and insert -- monoxide, --, therefor.

Signed and Sealed this  
Twenty-third Day of August, 2016

Michelle K. Lee  
*Director of the United States Patent and Trademark Office*

CERTIFICATE OF CORRECTION (continued)
U.S. Pat. No. 9,266,999 B2

Column 13
Line 26, Delete "tetrahydrorfuran" and insert -- tetrahydrofuran --, therefor.

Column 14
Line 50-51, Delete "R4CF$_2$CF(OC$_4$F$_8$SO$_2$F)x-[CH$_2$CF$_2$]y-R" and insert
-- R-[CF$_2$CF(OC$_4$F$_8$SO$_2$F)]x-[CH$_2$CF$_2$]y-R --, therefor.

Column 17
Line 30, Delete "that" and insert -- than --, therefor.

In the Claims

Column 19
Line 36, In Claim 6, delete "trom" and insert -- from --, therefor.

Column 20
Line 9, In Claim 7, delete "trom" and insert -- from --, therefor.